US006362383B1

(12) United States Patent
Wilmet et al.

(10) Patent No.: US 6,362,383 B1
(45) Date of Patent: Mar. 26, 2002

(54) HYDRO-FLUORINATION OF CHLORINATED HYDROCARBONS

(75) Inventors: Vincent Wilmet, Wavre; Francine Janssens, Vilvoorde, both of (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/623,345

(22) PCT Filed: Feb. 25, 1999

(86) PCT No.: PCT/BE99/00028

§ 371 Date: Sep. 29, 2000

§ 102(e) Date: Sep. 29, 2000

(87) PCT Pub. No.: WO99/43635

PCT Pub. Date: Sep. 2, 1999

(30) Foreign Application Priority Data

Feb. 26, 1998 (BE) .............................................. 9800150

(51) Int. Cl.⁷ ............................................... C07C 17/08
(52) U.S. Cl. ........................ 570/166; 570/167; 570/168; 570/169
(58) Field of Search ................................ 570/166, 167, 570/168, 169

(56) References Cited

U.S. PATENT DOCUMENTS 5,710,352 A * 1/1998 Tung ........................... 570/166

FOREIGN PATENT DOCUMENTS

| AU | 95/32.843 | 4/1996 |
|---|---|---|
| EP | 0 703 205 | 3/1996 |
| EP | 0 712 826 | 5/1996 |
| GB | 2 313 118 | 11/1997 |
| JP | 10/101593 | 4/1998 |
| WO | WO 95/27688 | 12/1995 |
| WO | WO 96/40605 | 12/1996 |
| WO | WO 9724307 | 7/1997 |

* cited by examiner

*Primary Examiner*—Alan Siegel
(74) *Attorney, Agent, or Firm*—Connolly Bove Lodge & Hutz LLP

(57) ABSTRACT

Improved process for the catalytic hydro-fluorination of saturated or unsaturated organic compounds corresponding to the general formula $C_wH_xCl_yF_z$ (I) in which w is an integer between 1 and 6, x is an integer between 0 and (2w+1) or between 0 and (2w−1), y is an integer between 1 and (2w+1) or between 1 and (2w−1), z is an integer between 0 and (2w+1) or between 0 and (2w−1) and the sum (x+y+z) is equal to (2w+2), comprising a continuous feed of hydrogen chloride.

Process for preparing 1,1,1,3,3-pentafluoropropane starting with 1,1,1,3,3-pentachloropropane, comprising two catalytic reaction steps, in which hydrogen chloride is preferably fed continuously into the reaction medium of at least one of the two reaction steps.

21 Claims, No Drawings

HYDRO-FLUORINATION OF CHLORINATED HYDROCARBONS

This application is a 371 of PCT/BE99/00028 filed Feb. 25, 1999.

The present invention relates to a process for the hydrofluorination of a chlorohydrocarbon by reaction with hydrogen fluoride in the presence of a hydrofluorination catalyst, and in particular to a process for the manufacture of 1,1,1,3,3-pentafluoropropane.

Liquid-phase hydrofluorination processes, based on the reaction of hydrogen fluoride and an organochlorine compound, in the presence of a catalyst, have been known for a long time. The desired products are organic compounds similar to the organochlorine compound used, in which the chlorine atoms have been partially or totally replaced with fluorine atoms. However, the degree of conversion of the reagents used is often low and the selectivity toward desired product is insufficient, in particular when a complete fluorination is desired. In certain cases, several steps are required in order to obtain the desired fluoro products. Thus, patent application WO 97/24307 discloses the two-step synthesis of 1,1,1,3,3-pentafluoropropane (HFC-245fa) starting with 1,1,1,3,3-pentachloropropane. The 1,1,1,3,3-pentachloropropane first reacts, in the gas phase, with hydrogen fluoride to give 1,1,1-trifluoro-3-chloro2-propene, which, after removal of the hydrogen chloride formed, reacts in a second step with hydrogen fluoride to give HFC-245fa.

It is consequently advantageous to have available an efficient hydrofluorination process allowing chlorine atoms to be replaced with fluorine atoms more easily and with high selectivity.

The term "hydrofluorination" means the addition reaction of hydrogen fluoride to a carbon-carbon double bond as well as the substitution reaction of a chlorine atom with a fluorine atom on a saturated substrate.

Consequently, the invention relates to a process for the hydrofluorination of a chlorohydrocarbon by reaction with hydrogen fluoride, in a reaction medium comprising a hydrofluorination catalyst, in which process hydrogen chloride is continuously fed into the reaction medium.

In the hydrofluorination process according to the present invention, the expression "continuous feed of hydrogen chloride" means the addition of hydrogen chloride into the reaction medium throughout the reaction, either in gaseous form or in liquid form, or in the form of any compound other than the reagents which is capable of generating hydrogen chloride in the reaction medium under the operating conditions selected.

In a continuous hydrofluorination process, the molar ratio between the hydrogen chloride added by continuous feed and the chlorohydrocarbon introduced continuously into the reactor is generally greater than or equal to 1. This molar ratio is advantageously greater than or equal to 3. However, this molar ratio is usually less than or equal to 100. This ratio is advantageously less than or equal to 50. In a particularly preferred manner, this ratio is greater than or equal to 5 and less than or equal to 25.

When the hydrofluorination process according to the invention is carried out in a batchwise manner, the hydrogen chloride can be fed in continuously, for example, by introducing a stream of hydrogen chloride gas into the reaction medium throughout the reaction. In this case, the hydrogen chloride feed rate is adjusted such that the ratio between the total amount of hydrogen chloride introduced throughout the reaction to the amount of chlorohydrocarbon initially used corresponds to the molar ratios indicated above.

The chlorohydrocarbon used in the hydrofluorination process according to the invention can be an aliphatic alkane corresponding to the general formula $C_wH_xCl_yF_z$ (I) in which w is an integer between 1 and 6, x is an integer between 0 and (2w+1), y is an integer between 1 and (2w+1), z is an integer between 0 and (2w+1) and the sum (x+y+z) is equal to (2w+2). The chlorohydrocarbon used in the process according to the invention is advantageously an aliphatic alkane corresponding to formula (I) in which w is an integer between 1 and 4 and x is an integer between 1 and 2w. As non-limiting examples of chloroalkanes used in the process according to the invention, mention may be made of dichloromethane, chlorofluoromethane, chlorodifluoromethane, 1-chloro-1-fluoroethane, 1,1-dichloro-1-fluoroethane and 1-chloro-1,1-difluoroethane, chlorotetrafluoroethane isomers, dichlorotrifluoroethane isomers, trichlorodifluoroethane isomers, tetrachlorofluoroethane isomers, pentachloroethane, compounds of general formula $C_3H_3Cl_{(5-z)}F_z$, $C_4H_5Cl_{(5-z)}F_z$ with z representing an integer which can take the values from 0 to 4.

The chlorohydrocarbon used in the hydrofluorination process according to the invention can also be an aliphatic alkene corresponding to the general formula $C_wH_xCl_yF_z$ (II) in which w is an integer between 1 and 6, x is an integer between 0 and (2w−1), y is an integer between 1 and (2w−1), z is an integer between 0 and (2w−1) and the sum (x+y+z) is equal to 2w. The chlorohydrocarbon used in the process according to the invention can also advantageously be an aliphatic alkene corresponding to the formula (I) in which w is an integer between 1 and 4. As non-limiting examples of chloroalkenes used in the process according to the invention, mention may be made of 1,1-dichloroethylene, trichloroethylene, perchloroethylene, vinyl chloride, 3,3,3-trichloro-1-propene, 1,1,3-trichloro-1-propene, 1,1,3,3,-tetra-chloro-1-butene, 1,1,1,3-tetrachloro-2-butene, 1,1,1,3 -tetrachloro-3-butene, 1,1,4,4,4-pentachloro-1-butene, 1,1,1,3-tetrachloro-2-propene, 1,1,3,3-tetrachlorol-1-propene, 1,1,3,3-tetrachloro-2-methyl-2-propene, 1,1,1,3-tetrachloro-2-methyl-2-propene and 1-chloro-3,3,3-trifluoropropene, as well as mixtures of these compounds.

One object of the invention is thus, starting with saturated or unsaturated chlorohydrocarbons, to produce fluoroalkanes or chlorofluoroalkanes which contain more fluorine atoms and fewer chlorine atoms than the reagents used. The invention is directed in particular toward the synthesis of fluorohydrocarbons or chlorofluorohydrocarbons such as, in particular, difluoromethane, pentafluoroethane, 1,1,1,2-tetrafluoroethane, 1,1,1-trifluoroethane, 1,1-difluoroethane, 1,2,2-trichloro-1,1-difluoroethane, 2,2-dichloro-1,1,1-trifluoroethane, 1,1,1-trifluoro-2-chloroethane, 1,1,1,3-tetrafluoro-3-chloropropane, 1,1,1,3,3-pentafluoropropane, 1,1,1,3,3-pentafluorobutane, 1,1,1,3,3,3-hexafluorobutane, 1,1,1,3,3-pentafluoro-2-methylpropane and 1,1,1,3,3,3-hexafluoropropane. The hydrofluorination process according to the invention is particularly suitable for preparing fluoroalkanes containing no chlorine atoms in their molecular structure, starting with saturated chlorohydrocarbons, as well as to the preparation of chlorofluoroalkanes starting with unsaturated chlorohydrocarbons.

In the hydrofluorination process according to the present invention, the reaction medium is advantageously in liquid form and the hydrofluorination catalyst contained therein is advantageously chosen from derivatives of metals from groups 3, 4, 5, 13, 14 and 15 of the Periodic Table of the Elements (IUPAC 1988) and mixtures thereof. The expression "derivatives of metals" means the hydroxides, oxides and inorganic salts of these metals, as well as mixtures thereof. Derivatives of titanium, niobium, tantalum, molybdenum, boron, tin and antimony are particularly selected. The catalyst is preferably chosen from derivatives of the metals from groups 4, 5, 14 and 15 of the Periodic Table of the Elements, and more particularly from derivatives of titanium, tantalum, tin and antimony. In the process according to the invention, the preferred metal derivatives are the salts of these metals, and the salts are preferably chosen from the halides, and more particularly from the chlorides, fluorides and chlorofluorides. Hydrofluorination catalysts that are particularly advantageous in the process according to the invention are the chlorides, fluorides and chlorofluorides of titanium, tin and antimony, in particular titanium tetrachloride, tin tetrachloride and antimony pentachloride. Catalysts comprising a titanium halide are preferred. Titanium tetrachloride alone or as a mixture with other catalysts is most particularly preferred, in particular in order to obtain 1,1,1,3,3-pentafluoropropane starting from 1,1,1,3,3-pentachloropropane or from 1-chloro-3,3,3-trifluoropropene.

The molar ratio between the catalyst and the chlorohydrocarbon in the reaction medium is generally greater than or equal to 0.001. It is preferably greater than or equal to 0.01. Very good results have been obtained in the presence of at least about 0.1 mol of catalyst per mole of chlorohydrocarbon. In principle, there is no upper limit to this ratio. For example, it can be up to 1000. It generally does not exceed 100. Usually, it does not exceed 10.

The molar ratio between the catalyst and the hydrogen fluoride in the reaction medium can vary within a wide range. It is generally greater than or equal to 0.001. It is preferably greater than or equal to 0.01. Very good results have been obtained in the presence of at least about 0.025 mol of catalyst per mole of hydrogen fluoride. In general, this ratio does not exceed 10. It usually does not exceed 1. Good results have been obtained with a ratio not exceeding 0.75.

The hydrofluorination process according to the present invention can be carried out in a continuous or batchwise manner. It is understood that the molar ratios above are expressed, in the case of a batchwise process, relative to the initial amounts of chlorohydrocarbon and hydrogen fluoride used, and, in the case of a continuous process, relative to the stationary amounts of chlorohydrocarbon and hydrogen fluoride in the reaction medium.

In the hydrofluorination process according to the invention, hydrogen fluoride in liquid or gaseous form and the chlorohydrocarbon, preferably in liquid form, are introduced into the reaction medium in a molar ratio generally of greater than or equal to 5. This molar ratio is preferably greater than or equal to 10. However, this molar ratio is usually less than or equal to 100. This molar ratio is advantageously less than or equal to 75 and preferably less than or equal to 50.

The hydrofluorination process according to the invention can be carried out within wide temperature and pressure ranges, which are preferably chosen so as to keep the reaction medium in liquid form. The process is generally performed at a temperature of at least 75° C. A temperature of at least 90° C. is preferred. A temperature of at least about 100° C. is particularly preferred. In a liquid-phase process, depending in particular on the admissible pressure, this temperature usually does not exceed about 160° C., temperatures of less than or equal to about 140° C. being especially recommended.

The process is generally performed at a pressure of at least about 2 bar. A pressure of at least about 10 bar is preferred. A pressure of at least about 15 bar is particularly preferred. This pressure usually does not exceed about 50 bar, pressures of less than or equal to about 30 bar being especially recommended.

The hydrofluorination process according to the invention can be carried out in any type of reactor or apparatus which is resistant to pressure, hydrogen fluoride and hydrogen chloride, and, in the case of a continuous process, which makes it possible permanently to maintain a substantially stable composition of the reaction medium. The hydrofluorination process according to the invention is usually carried out continuously in a reactor equipped with a device for adding reagents, in liquid or gas phase, and for removing a stream of gaseous products, for example in a reactor on which is mounted a column and a reflux condenser. This device makes it possible permanently to maintain a reaction medium composition which complies with the prescriptions outlined above, by appropriately adjusting the operating conditions (in particular the flow rates of the reagents entering the reactor, the temperature and pressure in the reactor and the temperature in the condenser).

Surprisingly, a continuous feed of hydrogen chloride into the reaction medium makes it possible to increase the chlorohydrocarbon conversion rate substantially, when the chlorohydrocarbon used is an aliphatic alkane of formula (I), to increase the selectivity toward totally fluorinated product and to reduce the accumulation of intermediate chlorofluoro compounds, which are optionally unsaturated, resulting from a partial replacement of the chlorine atoms of the chlorohydrocarbons and removal of the hydrogen halide (hydrogen chloride or fluoride) from the reagents or from the intermediate products formed.

The present invention also relates to a process for preparing 1,1,1,3,3-pentafluoropropane starting with 1,1,1,3,3-pentachloropropane, comprising two catalytic reaction steps, in which hydrogen chloride is preferably fed continuously into the reaction medium of at least one of the two reaction steps. This process makes it possible to produce 1,1,1,3,3-pentafluoropropane (HFC-245fa) in an industrially acceptable yield starting with 1,1,1,3,3-pentachloropropane (HCC-240fa).

A first variant—via 1-chloro-3,3,3-trifluoropropene—of the process for preparing 1,1,1,3,3-pentafluoropropane comprises:

a first reaction step in which 1,1,1,3,3-pentachloropropane (HCC-240fa) is reacted with hydrogen fluoride in liquid phase in the presence of a first hydrofluorination catalyst under conditions that are suitable for obtaining a mixture of reaction products comprising 1-chloro-3,3,3-trifluoropropene (HCFC-1233zd) in substantial amount, a second reaction step in which the 1-chloro-3,3,3-trifluoropropene (HCFC-1233zd) obtained from the first step is reacted with hydrogen fluoride in liquid phase in the presence of a second hydrofluorination catalyst, and preferably while hydrogen chloride is continuously fed in, in order to obtain 1,1,1,3,3-pentafluoropropane (HFC-245fa).

During or at the end of the first step, the volatile products in gaseous form are advantageously removed. The term "volatile products" means the HCFC-1233zd, the partially or totally fluorinated hydrocarbons that are more volatile than HCFC-1233zd, the hydrogen chloride coproduced, and the unreacted hydrogen fluoride.

In a first embodiment of this first variant, the 1-chloro-3,3,3-trifluoropropene (HCFC-1233zd) and the other partially or totally fluorinated volatile hydrocarbons obtained are separated from the volatile products removed during and/or after the first step and are used—without any other prior purification—in the second step to convert them into 1,1,1,3,3-pentafluoropropane (HFC-245fa). In other words, only the hydrogen chloride and hydrogen fluoride are removed from the mixture which will be used in the second step.

According to another embodiment of this first variant, which is a preferred embodiment, all the volatile products removed during and/or after the first step are used for the preparation of 1,1,1,3,3-pentafluoropropane (HFC-245fa) in the second step, i.e. not only the partially or totally fluorinated products, including the 1-chloro-3,3,3-trifluoropropene, but also the hydrogen chloride and hydrogen fluoride present in the reaction medium from the first step are used for the preparation of 1,1,1,3,3-pentafluoropropane (HFC-245fa) in the second step.

Similarly, during or at the end of the second step, the HFC-245fa and the products more volatile than the latter products are advantageously removed in gaseous form. After separation of the HFC-245fa, the other products removed—mainly the hydrogen chloride coproduced, the hydrogen fluoride and, optionally, certain partially fluorinated hydrocarbons entrained with the HFC-245fa—can be recycled into the process, preferably into the second reaction step.

Surprisingly, it has been discovered that by continuously feeding hydrogen chloride into a reaction medium containing 1-chloro-3,3,3-trifluoropropene (HCFC-1233zd) as chlorohydrocarbon, it is possible to substantially increase the rate of conversion of the HCFC-1233zd into 1,1,1,3,3-pentafluoropropane (HFC-245fa), to increase the selectivity of the reaction and to reduce the accumulation of intermediate chlorofluoro compounds. It was found to be particularly advantageous to send the hydrogen chloride coproduced during the first step into the second step, and/or to send some of the hydrogen chloride recovered after the second step back into the second step.

In this first variant, two different hydrofluorination catalysts are preferably used. Catalysts that are particularly suitable for preparing 1-chloro-3,3,3-trifluoropropene (HCFC-1233zd) from 1,1,1,3,3-pentachloropropane (HCC-240fa) and hydrogen fluoride in liquid phase comprise one or more of the following elements: titanium, tin, molybdenum and/or iron. Catalysts that are particularly suitable for preparing 1,1,1,3,3-pentafluoropropane (HFC-245fa) from 1-chloro-3,3,3-trifluoropropene (HCFC-1233zd) and hydrogen fluoride in liquid phase comprise one or more of the following elements: antimony, thallium, niobium. The catalysts are advantageously chosen from derivatives of the abovementioned metals, and mixtures thereof. The expression "derivatives of metals" means the hydroxides, oxides and inorganic salts of these metals, as well as mixtures thereof. The preferred derivatives of metals are the salts of these metals and these salts are preferably chosen from the halides, and more particularly from the chlorides, fluorides and chlorofluorides. Titanium tetrachloride, tin tetrachloride, molybdenum pentachloride and iron trichloride or alternatively a mixture of at least two of these products, in particular titanium tetrachloride alone or mixed with other catalysts, are most particularly preferred to obtain 1-chloro-3,3,3-trifluoropropene starting with 1,1,1,3,3-pentachloropropane. Antimony pentachloride, thalium pentachloride and niobium tetrachloride or a mixture of at least two of these products, in particular antimony pentachloride alone or mixed with other catalysts, are most particularly preferred to obtain 1,1,1,3,3-pentafluoropropane (HFC-245fa) starting with 1-chloro-3,3,3-trifluoropropene (HCFC-1233zd).

A second variant—via the dichlorotrifluoropropanes (HCFC-243) and 1,1,1,3-tetrafluoro-3-chloropropane (HCFC-244fa)—of the process for preparing 1,1,1,3,3-pentafluoropropane comprises:

a first reaction step in which 1,1,1,3,3-pentachloropropane (HCC-240fa) is reacted with hydrogen fluoride in liquid phase in the presence of a first hydrofluorination catalyst under suitable conditions—in particular with a continuous feed of hydrogen chloride—in order to obtain a mixture of reaction products consisting essentially (typically to more than 80% by weight) of saturated products, mainly dichlorotrifluoropropanes (HCFC-243), 1,1,1,3-tetrafluoro-3-chloropropane (HCFC-244fa) and 1,1,1,3,3-pentafluoropropane (HFC-245fa), a second reaction step in which the dichlorotrifluoropropanes (HCFC-243) and 1,1,1,3-tetrafluoro-3-chloropropane (HCFC-244fa) obtained during the first step are reacted with hydrogen fluoride, in liquid phase or in gas phase, in the presence of a second hydrofluorination catalyst in order to obtain 1,1,1,3,3-pentafluoropropane (HFC-245fa).

During or at the end of the first step, the volatile products in gaseous form are advantageously removed. In this second variant, the term "volatile products" essentially means the dichlorotrifluoropropanes (HCFC-243), the chlorotetrafluoropropanes and the HFC-245fa already formed in the first step, the hydrogen chloride coproduced and the unreacted hydrogen fluoride.

In a first embodiment of this second variant, the mixture of dichlorotrifluoropropanes and chlorotetrafluoropropanes is separated from the volatile products removed during and/or after the first step and they are used—without any other prior purification—in the second step to convert them into 1,1,1,3,3-penta-fluoropropane (HFC-245fa). In other words, the hydrogen chloride and hydrogen fluoride are removed from the mixture which will be used in the second step.

According to another embodiment of this second variant, all the volatile products removed during and/or after the first step are used for the preparation of 1,1,1,3,3-pentafluoropropane (HFC-245fa) in the second step, i.e. not only the partially or totally fluorinated products, including the dichlorotrifluoropropanes and chlorotetrafluoropropanes, but also the hydrogen chloride and hydrogen fluoride, and optionally also the HFC-245fa already formed in the reaction medium from the first step, are used as the mixture of reagents for the preparation of 1,1,1,3,3-pentafluoropropane (HFC-245fa) in the second step.

Similarly, during or at the end of the second step, the HFC-245fa and the products more volatile than the latter are advantageously removed in gaseous form. After separation of the HFC-245fa, the other products removed—mainly the hydrogen chloride coproduced, the hydrogen fluoride and optionally certain partially fluorinated hydrocarbons entrained with the HFC-245fa—can be recycled into the process, preferably into the second reaction step, except for the hydrogen chloride, which is preferably sent back into the first reaction step.

Surprisingly, it has been discovered that by continuously feeding hydrogen chloride into a reaction medium containing 1,1,1,3,3-pentachloropropane (HCC-240fa) as chlorohydrocarbon, it is possible to substantially increase the rate of conversion of the HCC-240fa, to increase the selectivity of the reaction toward saturated fluorinated products, such as 1,1,1-trifluoro-3,3-dichloropropane (HCFC-243fa), 1,1,1,3-tetrafluoro-3-chloropropane (HCFC-244fa) and 1,1,1,3,3-pentafluoropropane (HFC-245fa), to reduce the accumulation of relatively unreactive unsaturated compounds in the reaction medium, and to reduce the formation of heavy byproducts. It is consequently found to be particularly advantageous to send all or some of the hydrogen chloride coproduced during this first step back into the first step and/or to send some of the hydrogen chloride recovered after the second step back into the first step.

In this second variant, two different hydrofluorination catalysts are preferably used. Catalysts that are particularly suitable for preparing a mixture of mainly saturated reaction products from 1,1,1,3,3-pentachloropropane (HCC-240fa) and hydrogen fluoride in liquid phase comprise one or more of the following elements: titanium, tin, antimony, niobium and/or tantalum. With a continuous feed of hydrogen chloride, titanium-based catalysts are particularly suitable for use. Catalysts that are particularly suitable for the preparation of 1,1,1,3,3-pentafluoropropane (HFC-245fa) from HCFC-243 and HCFC-244 and hydrogen fluoride in liquid phase comprise one or more of the following elements: antimony, thallium, niobium. Catalysts that are particularly suitable for preparing 1,1,1,3,3-pentafluoropropane (HFC-245fa) from HCFC-243 and HCFC-244 and hydrogen fluoride in gas phase are, in particular, chromium-based catalysts.

The various reaction steps of the two variants of the process for preparing 1,1,1,3,3-pentafluoropropane can be carried out under conventionally-used operating conditions. For the steps in liquid phase, the process can typically be performed under the conditions described above in the context of the hydrofluorination process according to the invention.

The examples which follow illustrate the invention in a non-limiting manner.

In the examples below, the degree of conversion of the 1,1,1,3,3-pentachloropropane is the ratio, expressed as a percentage, between the amount used divided by the amount not converted at the end of the reaction and the amount used; the selectivity toward 1,1,1,3,3-pentafluoropropane is the ratio between the amount of 1,1,1,3,3-pentafluoropropane formed and the amount of 1,1,1,3,3-pentafluoropropane which would have been formed if all the 1,1,1,3,3-pentachloropropane converted had generated 1,1,1,3,3-pentafluoropropane. This is likewise the case for the selectivities toward trifluorochloropropene (HCFC-1233), dichlorotrifluoropropanes (HCFC-243) and chlorotetrafluoropropane (HCFC-244).

EXAMPLE 1

0.23 mol of 1,1,1,3,3-pentachloropropane, 0.04 mol of titanium tetrachloride and 9 mol of hydrogen fluoride were introduced into a 0.5 l stainless steel autoclave equipped with a mechanical paddle stirrer, a temperature probe and a dip tube for taking samples of liquid phase during the test. The autoclave was then immersed in a thermostatically regulated bath, maintained at a temperature of 120° C. with continuous stirring for 22 hours. Gaseous hydrogen chloride was introduced continuously into the autoclave at a flow rate of 0.2 mol/hour. The pressure was adjusted to 25 bar. A sample taken after reaction for 2.5 hours showed that the degree of conversion of the 1,1,1,3,3-pentachloropropane used was greater than 99 mol % with a selectivity toward HCFC-243 of 20.6%, toward HCFC-244 of 62.2%, toward HCFC-1233 of 3.3% and toward 1,1,1,3,3-pentafluoropropane of 11%. After reaction for 22 hours, the selectivity toward HCFC-243 was 13.9%, toward HCFC-244 was 41.9%, toward HCFC-1233 was 1.5% and toward 1,1,1,3,3-pentafluoropropane was 41.5%.

EXAMPLE 2

The test of Example 1 was repeated, but without a continuous feed of hydrogen chloride. A sample taken after reaction for 2.5 hours showed that the degree of conversion of the 1,1,1,3,3-pentachloropropane used was 77 mol % with a selectivity toward HCFC-243 of 0.1%, toward HCFC-244 of 8.7%, toward HCFC-1233 of 64.6% and toward 1,1,1,3,3-pentafluoropropane of 0.7%. After reaction for 22 hours, the degree of conversion of the 1,1,1,3,3-pentachloropropane was 99% and the selectivity toward HCFC-243 was 8.2%, toward HCFC-244 was 73.9%, toward HCFC-1233 was 11.9% and toward 1,1,1,3,3-pentafluoropropane was only 4.3%.

What is claimed is:

1. A process for the hydrofluorination of a chlorohydrocarbon by reaction with hydrogen fluoride in a reaction medium comprising a hydrofluorination catalyst, in which process hydrogen chloride is continuously fed into the reaction medium.

2. The process as claimed in claim 1, carried out in continuous mode, in which the molar ratio between the hydrogen chloride added by continuous feed and the chlorohydrocarbon introduced is greater than or equal to 1 and less than or equal to 100.

3. The process as claimed in claim 1, carried out in batchwise mode, in which the hydrogen chloride fed into the reaction medium is adjusted such that the ratio between the total amount of hydrogen chloride introduced throughout the reaction and the amount of chlorohydrocarbon initially used is greater than or equal to 1 and less than or equal to 100.

4. The process as claimed in claim 1, in which the chlorohydrocarbon is an aliphatic alkane corresponding to the general formula $C_wH_xCl_yF_z$ (I) in which w is an integer between 1 and 6, x is an integer between 0 and $(2w+1)$, y is an integer between 1 and $(2w+1)$, z is an integer between 0 and $(2w+1)$ and the sum $(x+y+z)$ is equal to $(2w+2)$.

5. The process as claimed in claim 1, in which the chlorohydrocarbon is an aliphatic alkene corresponding to the general formula $C_wH_xCl_yF_z$(I) in which w is an integer between 1 and 6, x is an integer between 0 and $(2w-1)$, y is an integer between 1 and $(2w-1)$, z is an integer between 0 and $(2w-1)$ and the sum $(x+y+z)$ is equal to $2w$.

6. The process as claimed in claim 1, wherein the process is carried out in liquid phase.

7. The process as claimed in claim 1, in which the reaction is carried out at a temperature of about 75 to 160° C., at a pressure of about 2 to 50 bar.

8. The process as claimed in claim 1, in which the molar ratio between the catalyst and the chlorohydrocarbon in the reaction medium is from 0.001 to 1000 and in which the molar ratio between the catalyst and the hydrogen fluoride in the reaction medium is from 0.001 to 10.

9. The hydrofluorination process as claimed in claim 1, applied to the manufacture of 1,1,1,3,3-pentafluoropropane by reaction between hydrogen fluoride and a chloro(fluoro)propane of general formula $CCl_{3-a}fa$—$CH_2$—$CHCl_{2-b}F_b$, in which a is a number from 0 to 3 and b is a number from 0 to 2.

10. The hydrofluorination process as claimed in claim 1, applied to the manufacture of 1,1,1,3,3-pentafluoropropane by reaction between hydrogen fluoride and 1-chloro-3,3,3-trifluoropropene.

11. The hydrofluorination process as claimed in claim 1, applied to the manufacture of a mixture of products consisting essentially of saturated products, mainly dichlorotrifluoropropanes (HCFC-243), 1,1,1,3-tetrafluoro-3-chloropropane (HCFC-244fa) and 1,1,1,3,3-pentafluoropropane (HFC-245fa), by reaction between hydrogen fluoride and 1,1,1,3,3-pentachloropropane.

12. A process for preparing 1,1,1,3,3-pentafluoropropane starting with 1,1,1,3,3-pentachloropropane, comprising two catalytic reaction steps, in which hydrogen chloride is fed continuously into the reaction medium of at least one of the two reaction steps.

13. A process for manufacturing 1,1,1,3,3-pentafluoropropane (HFC-245fa) comprising a first reaction step in which 1,1,1,3,3-pentachloropropane (HCC-240fa) is reacted with hydrogen fluoride in liquid phase in the presence of a first hydrofluorination catalyst under conditions that are suitable for obtaining a mixture of reaction products comprising 1-chloro-3,3,3-trifluoropropene (HCFC-1233zd) in substantial amount, a second reaction step in which the 1-chloro-3,3,3-trifluoropropene (HCFC-1233zd) obtained from the first step is reacted with hydrogen fluoride in liquid phase in the presence of a second hydrofluorination catalyst, in order to obtain 1,1,1,3,3,-pentafluoropropane (HFC-245fa).

14. The process as claimed in claim 13, in which chloro-3,3,3-trifluoropropene (HCFC-1233zd) and products more volatile than HCFC-1233zd are removed in gaseous form during or at the end of the first step.

15. The process as claimed in claim 14, in which all the volatile products removed during and/or after the first step are used for the preparation of 1,1,1,3,3-pentafluoropropane (HFC-245fa) in the second step.

16. The process as claimed in any one of claims 13 to 15, in which hydrogen chloride is introduced continuously into the reaction medium of the second step.

17. A process for manufacturing 1,1,1,3,3-pentafluoropropane (HFC-245fa) comprising a first reaction step in which 1,1,1,3,3-pentachloropropane (HCC-240fa) is reacted with hydrogen fluoride in liquid phase in the presence of a first hydrofluorination catalyst under suitable conditions—in particular with a continuous feed of hydrogen chloride—in order to obtain a mixture of reaction products consisting essentially of saturated products, mainly dichlorotrifluoropropanes (HCFC-243), 1,1,1,3-tetrafluoro-3-chloropropane (HCFC-244fa) and 1,1,1,3,3-pentafluoropropane (HFC-245fa), a second reaction step in which the dichlorotrifluoropropanes (HCFC-243) and 1,1,1,3-tetrafluoro-3-chloropropane (HCFC-244fa) obtained during the first step are reacted with hydrogen fluoride, in liquid phase or in gas phase, in the presence of a second hydrofluorination catalyst in order to obtain 1,1,1,3,3-pentafluoropropane (HFC-245fa).

18. The process as claimed in claim 17, in which dichlorotrifluoropropanes (HCFC-243) and products more volatile than the dichlorotrifluoropropanes are removed in gaseous form during or at the end of the first step.

19. The process as claimed in claim 17 in which hydrogen chloride is introduced continuously into the reaction medium of the first step.

20. The process as claimed in claims 17, in which the first step is carried out in the presence of a titanium-based catalyst.

21. The process as claimed in claim 13, wherein hydrogen chloride is continuously fed in the second reaction step.

* * * * *